United States Patent [19]

Labes

[11] 4,176,918
[45] Dec. 4, 1979

[54] FLUORESCENT LIQUID CRYSTAL DISPLAY

[75] Inventor: Mortimer M. Labes, Philadelphia, Pa.

[73] Assignee: Temple University, Philadelphia, Pa.

[21] Appl. No.: 851,393

[22] Filed: Nov. 14, 1977

[51] Int. Cl.$^2$ ............................ C09K 3/34; C02F 1/13
[52] U.S. Cl. ................................. 350/346; 252/299; 252/408; 350/349; 350/350
[58] Field of Search ................ 252/299, 408; 350/350, 350/349, 346

[56] References Cited

U.S. PATENT DOCUMENTS

| | | | |
|---|---|---|---|
| 3,844,637 | 10/1974 | Masi | 350/350 |
| 3,891,307 | 6/1975 | Tsukamoto et al. | 350/350 |
| 3,960,753 | 6/1976 | Larrabee | 252/299 |
| 3,975,286 | 8/1976 | Oh | 252/299 |

FOREIGN PATENT DOCUMENTS

| | | | |
|---|---|---|---|
| 2538865 | 3/1976 | Fed. Rep. of Germany | 252/299 |
| 1459046 | 12/1976 | United Kingdom | 252/299 |

OTHER PUBLICATIONS

Klanderman, B., et al., J. Am. Chem. Soc., vol. 97, No. 6, pp. 1585-1586 (1975).
Hamblen, D., et al., "Characteristics of an Electrically Controlled Fluorescent Dye Panel," IEEE Conference Record of 1972, Conference on Display Devices, N.Y., (Oct. 1972).
Baur, G., et al., Mol. Cryst. Liq. Cryst., vol. 22, pp. 261-269 (1973).
Sackmann, E., et al., Chem. Phys. Lett., vol. 4. No. 9, pp. 537-540 (1970).
Raynes, E. P., Electronics Lett., vol. 10, No. 9, pp. 141-142 (1974).
Ashford, A., et al., Electronics Lett., vol. 9, No. 5, pp. 118-120 (1973).
Lyle, S. J., et al., J.C.S. Dalton, pp. 1726-1729 (1972).
White, D. L., et al., J. Appl. Phys., vol. 45, No. 11, pp 4718-4723 (1974).

*Primary Examiner*—Benjamin R. Padgett
*Assistant Examiner*—T. S. Gron
*Attorney, Agent, or Firm*—Miller & Prestia

[57] ABSTRACT

A liquid crystal composition for improved electro-optic displays. The composition undergoes an electrically induced cholesteric-nematic phase transition and includes fluorescent materials which are excited by ultraviolet radiation. In the cholesteric phase of the composition, the fluorescence is much stronger producing sufficient contrast to render the display visible in the dark.

12 Claims, No Drawings

FLUORESCENT LIQUID CRYSTAL DISPLAY

BACKGROUND OF THE INVENTION

Liquid crystal displays are finding an increasing variety of applications. Heretofore, liquid crystal displays have been limited in visibility under lighting conditions other than those for which they were designed. A more versatile liquid crystal display which is easily discernible under various lighting conditions would definitely enhance the usefulness of the display as well as broaden its field of practical utilization. The present invention is directed to compositions for providing such displays and particularly for displays visible in the dark.

The background art includes U.S. Pat. No. 3,844,637 to Masi et al, in which a composition is disclosed. In that composition, a fluorescent material, known as a luminophor is mixed with a nematic liquid crystal material. This luminophor is any suitable organic fluorescent material. As stated at column 2, lines 38–42 of the Masi et al patent, however, "The molecules of the luminophor attach and align themselves with the molecules of the liquid crystal and have little or no optical effect in the absence of an electric field." The composition disclosed in the Masi et al patent also requires the use of a pair of polarizers to orient the transmission of light so as to maximize the contrast ratio. From this, it is clear that the Masi et al composition is limited to use with polarized light and to polar fluorescent additives.

U.S. Pat. No. 3,960,753 to Larrabee also relates to a composition including in one state at least a liquid crystal phase. Fluorescent additives, among which is a europium chelate, are also included but the fluorescence would appear only marginal in the liquid crystal phase. Larrabee's fluorescent material is in the dissolved state and according to Larrabee, its "visible fluorescent intensity is dependent upon the phase or orientation of the liquid crystal solvent". (Column 1, lines 7–10) But from the Larrabee data and the discussion in "Fluorescent Switching by Means of Liquid Crystals", *RCA Review*, Vol. 34, June, 1973, pp. 329–335, on the same topic, it seems clear that Larrabee's systems are suitable only for thermo-optic devices—i.e., devices in which a change in temperature induces the phase change which results in visible display.

More akin to the present invention is the display and display composition disclosed and patented by White and Taylor. (U.S. Pat. No. 3,833,287 and *Journal of Applied Physics*, Vol. 45, No. 11, pp. 4718, November 1974) When the display of White and Taylor is in the cholesteric (OFF) state, the guest dye molecules and the matrix absorb light of all polarizations; in the ON state much less light is absorbed because of the homeotropic alignment in which the long axis of the dye molecule and the matrix are perpendicular to the electric field vector and therefore have minimal absorption. Here again, the visibility of the display depends on the orientation of the dye molecules of the liquid crystal. Also, the dyes of White and Taylor are not fluorescent. Nevertheless, White and Taylor do use a cholesteric-nematic phase change induced by an electric field as a basis for a display.

The present invention similarly uses an electrically-induced cholesteric-nematic phase transition, but in combination with a fluorescent compound of strong emissivity. As distinct from Masi, Larrabee, and White and Taylor, polarization of the absorption of the guest fluorescent molecule is not required.

BRIEF DESCRIPTION OF THE INVENTION

The present invention is based upon a liquid crystal composition which undergoes an electrically induced cholestericnematic phase transition. The composition includes a fluorescent additive which is excited by ultraviolet light scattered strongly in the OFF state of the liquid crystal composition but not in the electrically induced state. Good contrast ratio in the light scattering characteristics of the composition is then produced and the composition is thus adapted for use in improved electro-optic displays, particularly for such displays which must be viewed in the dark. The fluorescent additive must be a compound which fluoresces and is soluble in the liquid crystal media and which significantly enhances the contrast ratio of the liquid crystal composition upon electrically induced phase transition, as viewed in the dark or under low ambient light conditions.

DESCRIPTION OF THE PREFERRED EMBODIMENT OF THE INVENTION

In its preferred embodiment, the composition of the present invention includes as the liquid crystal compositions p-n-pentyl-p'-cyanobiphenyl (CPB) doped with various chiral additives such as cholesteryl nonanoate (CN), cholesteryl chloride (CC) and the d-2-octyl ester of 4-(4-n-hexyloxybenzoyloxy)-benzoic acid. The preferred fluorescent guest molecule is a europium (III) chelate, particularly europium thenoyltrifluoroacetonate (EuTTA). With EuTTA in CN-CPB mixtures at various temperatures and cell thicknessess, a wide range of contrast ratios has been achieved as shown in the data of Table 1. In general, contrast ratio is a function of pitch as well as a function of the concentration of EuTTA, as shown in Table 1. Compositions of varying pitch and contrast ratios have been produced. The maximum contrast ratio in the foregoing composition obtained thus far is about 9.

DETAILED DESCRIPTION OF THE INVENTION

The present invention depends upon a cholesteric-nematic phase changing effect involving a fluorescent guest of strong emissivity but not necessarily showing a polarized absorption or emission. In such a composition, the off-state is more absorbing of the exciting radiation than the on-state. Thus emission in the off-state is very intense and is reduced in the non-scattering on-state by ratios as high as 9:1. As compared to prior art fluorescent additives in liquid crystal compositions, the additives in the present invention need not have polarized absorptions or emissions. Indeed, the europium$^{+3}$ chelates used in the preferred embodiment of the present invention have symmetrical ligands distributed around the core ion and have little or no polarization of either absorption or emission. Such compounds are known, however, to interact strongly with organic molecules and have been used, for example, in NMR spectroscopy as "shift reagents". The EuTTA used in the preferred embodiment of the present invention fluoresces intensely with a peak radiation at about 612 nm, when excited with uv, with an excitation maximum at about 360 nm. Other additives may also be used, such as terbium (III) chelates which have a green fluorescence. Referring particularly to the composition of the preferred embodiment of the present invention, it should be noted that CPB alone is fluorescent, excitation between 240 and 360 nm producing fluorescence between 330 and 450 nm, with the maximum at 370 nm. However, in CPB alone there is significant polarization of the fluorescence between homogeneously and homeotropically aligned CPB. Because of the fluorescence intensity, wavelength and contrast ratio in CPB alone, it is not suitable for display.

CPB containing EuTTA may be switched electrically from a homogeneous to a homeotropic configuration but little or no contrast is observed in the red fluorescence.

Modification of this composition by the addition of a cholesteric molecule such as CN causes intense scattering of incident light in the initial off-state, demonstrating the necessity of the cholesteric-nematic phase change as the basis of the high contrast ratios obtainable in the compositions of the present invention.

In evaluating compositions used in the present invention, cells constructed from tin-oxide coated glass with Mylar spacers are placed in a temperature-controlled brass cell housing of conventional design, as described for example in the *Journal of Chemistry and Physics*, Vol. 56, Pages 3308 (1972) by Teucher, Ko and Labes. In evaluating the present invention, fluorescence was observed in both transmissive and reflective modes. In the reflective mode, incident exciting light (from either a Xenon lamp through a Bausch & Lomb grating monochromator with a band width of about 15 nm or a long wave uv lamp from Edmund Scientific) made an angle of 60° with the sample surface, and fluorescence was measured at an angle of 30° from the surface with a Heath monochromator (EU-700) and an RCA IP21 photomultiplier.

By way of illustration, results for various concentrations of EuTTA in CN-CPB mixtures at various temperatures and cell thicknesses are given in Table 1. As would be expected, contrast ratio varies as a function of pitch and the concentration of EuTTA. Driving characteristics are typical of those of any cholestericnematic device, that is the smaller the pitch (P) the higher the critical field ($E_c$) required, in accordance with known relations.

In general, the nematic material used in the present invention should not have significant uv absorption and should be uv stable. Examples are: p-alkyl- or p-alkoxy-p'-cyanobiphenyls and mixtures thereof; the cyano-, alkyl, and alkoxyl-substituted phenyl cyclohexanes, e.g.,

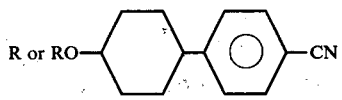

substituted benzoyl and benzoyloxybenzoate esters and mixtures thereof; 4-(trans-4-alkyl or alkyloxycyclohexyl) carboxylic acids and mixtures thereof; alkyl and alkyloxybenzoic acids or mixtures thereof. Combinations of the above are also possible. In all of the foregoing, the alkyl and alkoxyl group (represented by "R" and "RO") should comprise no more than ten carbons.

These liquid crystals are made cholesteric by the addition of any chiral compound, preferably a chiral nematogenic compound such as one of the optical isomers of

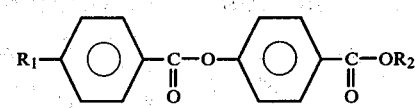

wherein $R_1$ contains 1 to 10 carbon atoms, and $R_2$ is an optically active branched alkyl chain varying from 1 to 10 carbon atoms, (a specific example of which may contain $R_1$ being $C_6H_{13}O$, and $R_2$ being

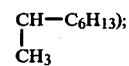

or a cholesteric compound chosen from the group consisting of (a) 1–10 carbon atom-alkanoic acid esters of cholesterol, and (b) cholesteryl halides, nitrates or sulfoxides or cholesteryl alkyl carbonates or thioesters in which the alkyl includes 1–10 carbon atoms.

The fluorescent additive or guest in the compositions of the present invention generally comprises any compatible fluorescent material which is soluble and fluorescent in the liquid crystal phase. A class which is believed to contain many such useful compositions is rare earth metal β-diketones and salts thereof. Useful chelates, within this class can be represented by the formula $M(Lig)_3$ where M represents a metal of the rare earth series such as those elements having an atomic number of 57–71 and 89–103 inclusive (i.e., the lanthanides and the actinides) and Lig represents a β-diketone ligand moiety which can broadly be referred to as a 1,3-dioxocarbonyl moiety. The ligand moieties can be alike or different and they are all linked in chelate form to the rare earth metal. A more detailed structural representation of useful chelates is as follows:

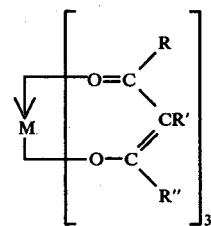

wherein M has its previously described meaning and R, R', and R", which can be alike or different, are monovalent hydrocarbon radicals, e.g., alkyl, aryl, alkaryl, aralkyl, cycloalkyl, halohydrocarbon (preferably fluorocarbon) or heterocyclic radicals generally of no more than 10–12 carbons each and free of aliphatic unsaturation; R' can also be chlorine, bromine, iodine or cyano.

The groups R, R' and R" can also be substituted with noninterfering functional substituents such as one or more halogens of atomic number from 9–53, inclusive; one or more hydrocarbon substituents of the types just defined; one or more hydrocarbyl ether or thioether substituents wherein the hydrocarbon moiety is as just defined; one or more hydrocarbyloxy-carbonyl, i.e., carboxyester, substituent or mono- or dihydro- carbylaminocarbonyl, i.e., carboxamido, substituents wherein in all three types the hydrocarbyl substituents are as just defined; and one or more hydrocarbylcarbonyl or thiocarbonyl substituents wherein the hydrocarbyl radicals are as just defined.

The rare earth metal unit in the useful chelates can be any one of the rare earth metals which are normally regarded as being members of the lanthanide or actinide series and are expressly inclusive of the transition rare earth metals running from atomic numbers 57–71 and 89–103, such as lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, berkelium, californium, einsteinium, fermium, medelevium, nobelium, and lawrencium. Especially preferred rare earth metals include europium and terbium.

The ligand moieties of the useful rare earth metal chelates can also vary widely and include compounds of the basic structure:

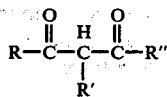

wherein R, R' and R" radicals have their previously defined meanings. Suitable classes of useful ligands include dialkyl β-diketones, e.g., pentane-2,4-dione, 2-methylpentane-2,4-dione, hexane-2,4-dione, heptane-2,4-dione, heptane-3,5-dione, nonadecane-9,11-dione, 9-methyloctadecane-8,10-dione, tricosane-11,13-dione; 1,1,1,5,5,5-hexafluoropentane-2,4-dione, 1,1,1-trifluoropentane-2,4-dione, 1,1,1,2,2,3,3,3-heptafluoro-7,7-dimethyl-4,6-octanedione, 1,1,1,19,19,19-hexafluorononadecane-9,11-dione; alkylaryl β-diketones, e.g., 1-phenylbutane-1,3-dione, 1-phenyl-4,4,4-trifluorobutane-1,3-dione, 1-phenylundecane-1,3-dione, 1-(3,4-dimethylphenyl)-2-methyltridecane-1,3-dione, 1-(4-methoxyphenyl)-4,4,4-trifluorobutane-1,3-dione, 1(4-nitrophenyl)-4,4,4-trifluorobutane-1,3-dione, 1-(3-nitrophenyl)-4,4,4-trifluorobutane-1,3-dione, 1-phenyl-2-trifluoromethyl-4,4,4-trifluorobutane-1,3-dione; 1-furylbutane-1,3-dione, 1-thienylbutane-1,3dione, 1-furyl-3-phenylpropane1,3-dione, and diaryl β-diketones, e.g., 1,3-diphenylpropane-1,3-dione, 1,3-(2,4-dimethylphenyl) propane-1,3-dione, 1-phenyl-3-(2-pyridyl)propane-1,3-dione, 1,3-di(4-pyridyl)propane-1,3-dione, 1-(4-methoxy)-3-(4-nitrophenyl)propane-1,3-dione, 1,3-di(4-nitrophenyl)propane-1,3-dione, 1,3-difurylpropane-1,3-dione, 1-furyl-3-thienylpropane-1,3-dione, 1,3-difurylpropane-1,3-dione, and 1,3-dithienylpropane-1,3-dione.

The size of the particular ligand(s) used has an effect on the efficiency of the system. The ligand moieties absorb the ultra-violet radiation and transmit the energy to the rare earth metal which fluoresces. Thus, larger ligands can increase the efficiency by absorbing more ultra-violet radiation. Also, as the ligand determines the absorption maximum of the system, various chelates can be tailor-made to absorb at various wavelengths.

Compounds from the foregoing group which have been demonstrated to be useful in the present invention are: tris[4,4,4-trifluoro-1-(2-thienyl)-1,3-butanediono]-europium (EuTTA, europium thenoyltrifluoroacetonate) and hydrates thereof, and tris[1,1,1,2,2,3,3,3-heptafluoro-7,7-dimethyl-4,6-octanediono]-europium. Tris [4,4,4-trifluoro-1-(2-thienyl)-1,3butanediono]-terbium has also been tested but found unsatisfactory because of its loss of fluorescence in the liquid crystal media. Tris [1-phenylbutane-1,3,diono]-terbium (terbium(III) benzoylacetonate) was found to fluoresce in liquid crystal media albeit not as strongly as EuTTA. Typical solubilities of such compounds in liquid crystal compositions of the present invention are of the order of 3–5%.

Other types of fluorescent compounds which may be useful in the present invention are hydrocarbons of the linear aromatic rings series, such as terphenyl, quaterphenyl, quinquephenyl, sexiphenyl, and their derivatives. Of this group, quaterphenyl, quinquephenyl and sexiphenyl have been successfully demonstrated.

Following is a specific example of the present invention. A numeric display cell with a 25 micron spacer was assembled in the laboratory with a composition consisting of 0.05% by weight of tris[4,4,4-trifluoro-1-(2-thienyl)-1,3-butanediono] europium in a 26% cholesteryl nonanoate—74% p-n-pentyl-p'-cyanobiphenyl solvent. This cell was addressed with an ac signal of 1000 Hz, 50 v rms. With no illumination, the cell displayed characteristics typical of a cholesteric-nematic phase transition device. When illuminated with long wave uv excitation (peak excitation at 350 nm) the device in the off-state showed a brilliant red-pink fluorescence (peak emission at 612 nm). When addressed, the numeric fluorescence showed a weak fluorescence in a brilliant background of strong fluorescence with a contrast ratio of about 9:1 and an on-off response time of about 100 milliseconds.

By way of further exemplifying the present invention, contrast ratio, and other variables have been observed over a wide range of parameters, under conditions similar to that described above. The resulting data is reproduced in Table 1.

TABLE 1

Variations of Contrast Ratio of EuTTA in CN-CPB with Concentration, Temperature, Pitch and Thickness

| CN wt % | EuTTA wt % | Temp. °C. | Pitch μm | Thickness μm | Contrast Ratio (off/on) |
|---|---|---|---|---|---|
| 11.0 | 1.0 | 24 | 1.6 | 23.4 | 2 |
| 11.0 | 0.6 | 24 | 1.6 | 12.7 | 2 |
| 11.0 | 0.5 | 24 | 1.6 | 23.4 | 2 |
| 11.0 | 0.1 | 24 | 1.6 | 23.4 | 3 |
| 11.0 | 0.05 | 24 | 1.6 | 23.4 | 4 |
| 21.3 | 0.7 | 24 | 0.7 | 50.8 | 3 |
| 21.3 | 0.46 | 24 | 0.7 | 23.4 | 4 |
| 21.3 | 0.22 | 24 | 0.7 | 23.4 | 5 |
| 21.3 | 0.11 | 24 | 0.7 | 23.4 | 7 |
| 21.3 | 0.06 | 24 | 0.7 | 23.4 | 7 |
| 26.0 | 1.0 | 24 | 0.6 | 50.8 | 4 |
| 26.0 | 1.0 | 24 | 0.6 | 23.4 | 4 |
| 26.0 | 0.2 | 22 | 0.6 | 23.4 | 5 |
| 26.0 | 0.2 | 10 | 0.6 | 23.4 | 6 |
| 26.0 | 0.1 | 24 | 0.6 | 23.4 | 7 |
| 26.0 | 0.1 | 10 | 0.6 | 23.4 | 8 |
| 26.0 | 0.05 | 25 | 0.6 | 23.4 | 8 |
| 26.0 | 0.05 | 22 | 0.6 | 23.4 | 9 |
| 26.0 | 0.05 | 10 | 0.6 | 23.4 | 9 |
| 31.3 | 0.5 | 24 | 0.4 | 23.4 | 4 |
| 31.3 | 0.1 | 24 | 0.4 | 23.4 | 6 |

Although this invention has been described with reference to specific examples and embodiments, it is not limited thereto. Variations in proportions and compounds used may be made by those skilled in the art without departing from the true spirit and scope of this invention, and it is intended therefore that the definition of the invention is the appended claims should be construed accordingly.

Having now described my invention, I claim, and desire to secure by Letters Patent, the following:

1. Liquid crystal composition adapted to produce high contrast ratio electrically induced light displays, comprising a liquid crystal mixture including a nematic liquid crystal solvent and a cholesteric or chiral nematogenic compound, which mixture is stable when exposed to ultraviolet radiation and which is adapted to undergo a reversible electrically induced phase transition from a normal cholesteric phase, in which incident ultraviolet radiation is scattered, to an electrically induced nematic phase, in which incident ultraviolet radiation scattering is substantially reduced as compared to the cholesteric phase scattering, said composition further including a sufficient amount of a fluorescent compound, which is soluble in said mixture, which is excited by ultraviolet light scattered strongly in the cholesteric phase of the mixture but not in the electrically induced nematic state, and which significantly enhances the contrast ratio of the liquid crystal composition upon electrically induced phase transition, as viewed in the dark or under low ambient light conditions.

2. Composition, as recited in claim 1, wherein said liquid crystal mixture comprises a solvent selected from the group consisting of p-alkyl- or p-alkoxy-p'-cyanobiphenyls and mixtures thereof.

3. Composition, as recited in claim 1, wherein said chiral nematogenic compound consists of one or more optical isomers of

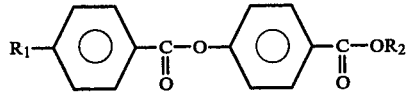

wherein $R_1$ contains 1 to 10 carbon atoms, and $R_2$ is an optically active branched alkyl chain varying from 1 to 10 carbon atoms, and said cholesteric compound is selected from the group consisting of 1–10 carbon atom-alkanoic acid esters of cholesterol, cholesteryl halides, cholesteryl nitrates, alkyl cholesteryl sulfoxides, cholesteryl alkyl carbonates, and cholesteryl thioesters in which the alkyl includes 1–10 carbon atoms.

4. Composition, as recited in claim 1, wherein said mixture comprises p-n-pentyl-p'-cyanobiphenyl with cholesteryl nonanoate or the d-2-octyl ester of 4-(4-n-hexyloxybenzoyloxy)-benzoic acid.

5. Composition, as recited in claim 1, wherein said mixture comprises 11–31.3 weight % cholesteryl nonanoate 0.05–5% tris [4,4,4-trifluoro-1(2-thienyl)-1,3-butanediono] europium and remainder p-n-pentyl-p'-cyanobiphenyl.

6. Composition, as recited in claim 1, wherein said fluorescent compound consists of europium thenoyltrifluoroacetonate.

7. Composition, as recited in claim 1, wherein said fluorescent compound consists of tris[1,1,1,2,2,3,3-heptafluoro7,7-dimethyl-4,6-octanediono]-europium.

8. Composition, as recited in claim 1, wherein said fluorescent compound is terbium (III) benzoylacetonate.

9. Composition, as recited in claim 1, wherein said fluorescent compound consists of one or more rare earth metal chelates.

10. Composition, as recited in claim 1, wherein said fluorescent compounds consists of a europium or terbium chelate.

11. Composition, as recited in claim 1, wherein said fluorescent compound consists of a linear aromatic compound from the group consisting of terphenyl, quarterphenyl, quinquephenyl, sexiphenyl and derivatives thereof.

12. An electric field cholesteric to nematic phase change display device in which is incorporated the liquid crystal composition recited in claim 1.

* * * * *